United States Patent
Rudzinskaya

(10) Patent No.: US 12,144,760 B2
(45) Date of Patent: Nov. 19, 2024

(54) POSTURE ENHANCING TOP

(71) Applicant: Krystsina Rudzinskaya, Tiburon, CA (US)

(72) Inventor: Krystsina Rudzinskaya, Tiburon, CA (US)

(73) Assignee: Wear Etalon Corporation, Tiburon, CA (US)

( * ) Notice: Subject to any disclaimer, the term of this patent is extended or adjusted under 35 U.S.C. 154(b) by 0 days.

(21) Appl. No.: 17/567,450

(22) Filed: Jan. 3, 2022

(65) Prior Publication Data

US 2023/0210206 A1   Jul. 6, 2023

(51) Int. Cl.
*A61F 5/00* (2006.01)
*A61F 5/02* (2006.01)

(52) U.S. Cl.
CPC .................... *A61F 5/026* (2013.01)

(58) Field of Classification Search
CPC .... A61F 5/026; A61F 5/02; A61F 5/03; A61F 5/028; A61F 5/37; A61H 1/0281; A61H 1/0292; A61H 1/008; A41C 3/0057; A41C 3/0021; A41C 3/0028; A41C 3/005; A41D 13/0512
USPC .......................................................... 602/19
See application file for complete search history.

(56) References Cited

U.S. PATENT DOCUMENTS

| | | | | |
|---|---|---|---|---|
| 1,581,791 A | * | 4/1926 | Davison | A61F 5/026 2/331 |
| 2009/0126084 A1 | * | 5/2009 | Fenske | A61F 5/026 2/243.1 |
| 2010/0010568 A1 | * | 1/2010 | Brown | A61H 1/008 2/69 |
| 2011/0237993 A1 | * | 9/2011 | Kirk | A61F 5/026 602/20 |
| 2013/0296756 A1 | * | 11/2013 | Troncoso | A61F 5/02 602/19 |
| 2014/0317826 A1 | * | 10/2014 | Decker | A41D 13/0015 2/69 |
| 2017/0273365 A1 | * | 9/2017 | Muhlenfeld | A41C 3/0028 |
| 2017/0354530 A1 | * | 12/2017 | Shagdar | A41D 31/18 |
| 2019/0029866 A1 | * | 1/2019 | Stier | A61F 5/026 |

* cited by examiner

*Primary Examiner* — Adam Baker
(74) *Attorney, Agent, or Firm* — My Patent Guys; Christopher Pilling

(57) ABSTRACT

A posture enhancing top is provided, either as a stand-alone garment or a top configured to be integrated with an existing garment. The top includes a front portion and a pair of shoulder members configured to cover and engage a wearer's shoulders. A central spine member is configured to be positioned along the wearer's spine. Adjustable straps are attached to the central spine member and shoulder members. The straps and shoulder members are configured to pull the wearer's shoulders backwardly and downwardly towards the wearer's spine improving the wearer's posture. Slits positioned on the straps provide a tool to increase the pulling force over a predetermined amount of time providing a training regimen for the use of the posture enhancing top.

7 Claims, 9 Drawing Sheets

FRONT

FRONT

BACK

POSTURE ENHANCING TOP

CROSS-REFERENCE TO RELATED APPLICATIONS

N/A

BACKGROUND OF THE INVENTION

1. Field of the Invention

The present invention generally relates to garments to improve posture, but more particularly to posture enhancing upper body garments.

2. Description of Related Art

Posture is an overall body alignment from the bottom of our feet to the crown of our head. Human bodies function best in the ideal (or standard) posture and have a significant amount of strain and stress in poor alignment. The most common type of poor postures, such as slouching, occurs when the shoulders, upper thoracic spine and neck move forward. Our invention focuses on solving slouching problems and supporting postoperative patients during their recovery.

Injuries, habits such as technology, use of phones, repetitive daily activities, sitting jobs; muscle weakness, low confidence, aging, genetics or body changes such as pregnancy when the center of gravity shifts and body recalibrates its alignment to allow for the change, lead to poor posture.

Poor posture can lead to a variety of physical, psychological, and financial problems. Physical problems include back pain, headache, shallow breathing, worsened digestion, hormonal imbalance, blood circulation issues, and proneness to injuries and strains. Psychological problems encompass stress, lower confidence, decreased focus, pessimism. Poor posture therefore may result in high financial costs for individuals and society.

Currently, there are solutions and products that attempt to address the posture concerns discussed above. Posture correctors with straps on shoulders are very common. The straps pull shoulders posteriorly and, as a result, significantly limit the wearer's movement in the shoulder joint. Posture correctors with a cueing design provide more gentle support and allow for the wearer's body to move freely. This type of corrector works for people with strong back muscles that can hold their back upright and just need some occasional reminding. However, people with weak back muscles that have difficulty holding their postures easily fight the gentle garment resistance and slide back into their poor postural patterns.

Reminders work for some people, however, due to the informational and notification overload people get overwhelmed with reminders and slide back into their poor postural habits. Though many posture correctors serve their function to improve posture, they lack aesthetic appeal, which makes wearing less desirable and less consistent to achieve successful results. Further, there is no solution that gradually develops muscle strength and memory holistically, so that the body learns to remember and hold the upright position; and that is easily integrated into common garments, which are aesthetically pleasing and enjoyable so that healthy postural habits can be developed and maintained in regular populations and in postoperative patients. Consequently, a solution is needed.

BRIEF SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

It is an object of the present invention to provide a posture enhancing technology that can be integrated into upper-body garments that are configured to be used for general posture improvement, scoliosis adjustment, posture maintenance, or recovery in postoperative patients.

It is another object of the present invention to provide a posture enhancing technology that is configured to integrate into any upper garment to correct the wearer's posture.

In order to do so, a posture enhancing top is provided, comprising a pair of top shoulder members; a pair of lower shoulder members, wherein the pair of top shoulder members and the pair of lower shoulder members are configured to cover and engage a wearer's scapulae, a lower horizontal band configured to encircle the wearer's torso; a central spine member extending vertically from the lower horizontal band, wherein the central spine member is configured to be positioned along the wearer's spine; and, a plurality of straps attached to the central spine member and a top shoulder member of the pair of top shoulder members and a lower shoulder member of the pair of lower shoulder members, wherein each strap of the plurality of straps is adjustable in length such that the length between the central spine member and the pair of top shoulder members and the pair of lower shoulder members is configured to be reduced via a pulling force of the wearer's shoulders backwardly and downwardly towards the wearer's spine improving the wearer's posture.

In one embodiment, the pair of top shoulder members, the pair of lower shoulder members, and the lower horizontal band are constructed from an elastic material. In one embodiment, the central spine member and the plurality of straps are constructed from a non-elastic material. In one embodiment, the central spine member is constructed of several layers of non-elastic material forming a rigid element configured to counterbalance the pulling force from the plurality of straps. In one design version, the plurality of straps comprises an upper left strap, an upper right strap, a middle left strap, a middle right strap, a lower left strap, and a lower right strap. In another design version, the upper left strap and the upper right strap are positioned at an upper part of the scapula creating an anatomically correct backwardly and downwardly pulling force, while the middle left strap, the middle right strap, the lower left strap and the lower right strap contribute to reinforcing the pulling force of the upper left strap and the upper right strap. In another design, the upper left strap and the upper right strap are attached to each respective shoulder member of the pair of top shoulder members, and the middle left strap, the middle right strap, the lower left strap and the lower right strap are attached to each respective shoulder member of the pair of lower shoulder members. In yet another design, each strap of the plurality of straps comprises a number of slits configured to enable the adjustment in length of each strap. In one embodiment, a front portion is provided, wherein the front portion connected to the pair of top shoulder members, the pair of lower shoulder members, and the lower horizontal band, wherein the front portion includes an opening and fastener enabling the wearer to take on and off the posture enhancing top. In one embodiment, the front portion is constructed from an elastic material. In another embodiment, the plurality of straps comprises an upper left strap, an upper right strap, a middle left strap and a middle right strap. In one embodiment, the upper left strap and the upper right strap are angled upwards towards the pair of top shoulder members from the central spine member and the middle left strap and the middle right strap extend from the central spine member to the pair of lower shoulder members. In one embodiment, the upper left strap and the upper right strap are angled upwards towards the pair of top shoulder members from the central spine member, the middle left strap and the middle right strap extend from the central spine member to the pair of lower shoulder members, and the lower left strap and the lower right strap are angled downwardly from the central spine member to the pair of lower shoulder members.

In another aspect of the invention, a posture enhancing top is provided, comprising a pair of top shoulder members; a pair of lower shoulder members, wherein the pair of top shoulder members and the pair of lower shoulder members are configured to cover and engage a wearers shoulders; a central spine member positioning along the wearer's spine; a plurality of straps attached to the central spine member and a top shoulder member of the pair of top shoulder members and a lower shoulder member of the pair of lower shoulder members, wherein each strap of the plurality of straps is adjustable in length such that the length between the central spine member and the pair of top shoulder members and the pair of lower shoulder members is configured to be reduced via a pulling force of the wearer's shoulders backwardly and downwardly towards the wearer's spine improving the wearer's posture, wherein the plurality of straps comprises of an upper left strap, an upper right strap, a middle left strap, and a middle right strap; and, the upper left strap and the upper right strap are angled upwards towards the pair of top shoulder members from the central spine member and the middle left strap and the middle right strap extend from the central spine member to the pair of lower shoulder members.

The foregoing has outlined rather broadly the more pertinent and important features of the present disclosure so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present disclosure. It should be realized by those skilled in the art that such equivalent structures do not depart from the spirit and scope of the invention as set forth in the appended claims.

BRIEF DESCRIPTION OF THE SEVERAL VIEWS OF THE DRAWINGS

Other features and advantages of the present invention will become apparent when the following detailed description is read in conjunction with the accompanying drawings, in which.

DETAILED DESCRIPTION OF EMBODIMENTS OF THE INVENTION

Figure 1:
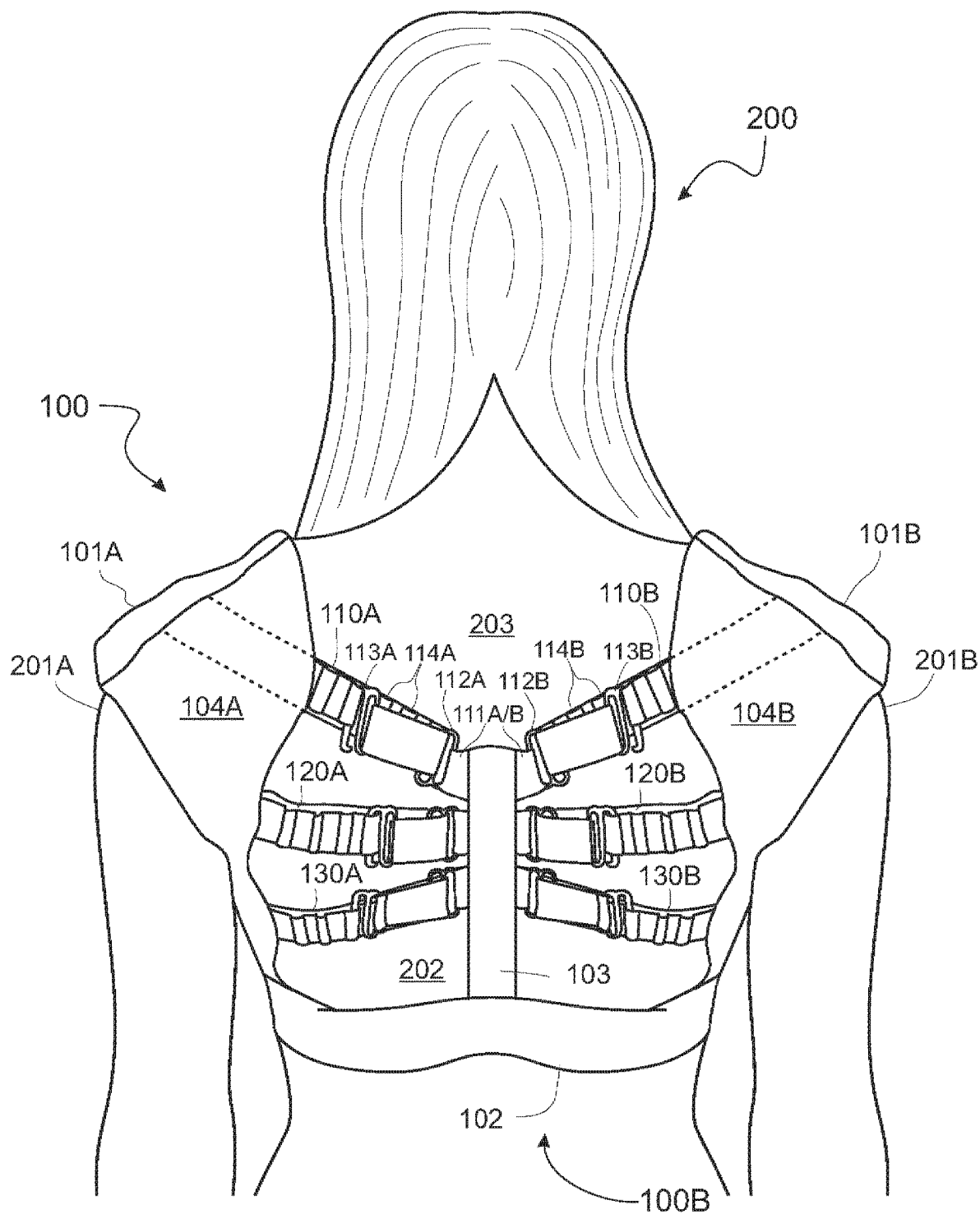
FIG. 1 is a back view of a posture-enhancing top according to an embodiment of the present invention.

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein to specifically provide a posture enhancing top.

As used herein, the singular forms "a," "an," and "the" include plural references unless the context clearly dictates otherwise. Any reference to "or" herein is intended to encompass "and/or" unless otherwise stated. As used herein, the term "about" or "approximately" refers to an amount that is near the stated amount by about 0%, 5%, or 10%, including increments therein. Alternatively, the term "about" or "approximately" refers to a range of values within plus or minus 10% of the specified number. As used in this application, the term "substantially" means that the actual value is within about 10% of the actual desired value, particularly within about 5% of the actual desired value and especially within about 1% of the actual desired value of any variable, element or limit set forth herein. As used herein, the term "attached to" refers to direct attachment or attachment via one or more additional elements.

FIGS. 1-4 are various views of a posture enhancing top according to an embodiment of the present invention. Referring now to FIGS. 1-4, the posture enhancing top 100 is illustrated and includes a front side 100A and back side 100B. In some embodiments, the posture enhancing top 100 comprises a pair of top shoulder members 101A and 101B and a pair of lower shoulder members 104A and 104B configured to cover the left 201A and right shoulder 201B of the wearer 200 respectively, wherein each shoulder member of the pair of shoulder members extend from the front side to the back side of the posture enhancing top. In some embodiments, the posture enhancing top 100 further comprises a lower horizontal band 102 and central spine member 103. In one embodiment, the pair of shoulder members (top and lower), and the lower horizontal band, as well as the front portion of the posture enhancing top, are constructed from an elastic fabric. In one embodiment, the lower horizontal band 102 is positioned around the middle/low-middle portion 202 of the wearer's back and the central spine member 103 extends from the lower horizontal band 102 to the upper middle portion 203 of the wearer's back. In alternative embodiments, the horizontal band is not provided. The positions of these components affect the placement and positioning of the plurality of straps, which will be described in greater detail below.

In one embodiment, the posture enhancing top 100 comprises a plurality of straps extending from the central spine member 103 towards the pair of top shoulder members 101A and 101B and lower shoulder members 104A and 104B. More specifically, the plurality straps comprise a pair of upper straps 110A and 110B, a pair of middle straps 120A and 120B, and a pair of lower straps 130A and 130B, wherein each strap of each pair extends towards its respective shoulder member A to A and B to B. Each pair of straps of the upper straps, middle straps, and lower straps have similar construction and will be discussed below using the upper straps as an example, but it should be understood that the details apply to the middle and lower straps as well.

Figure 2:
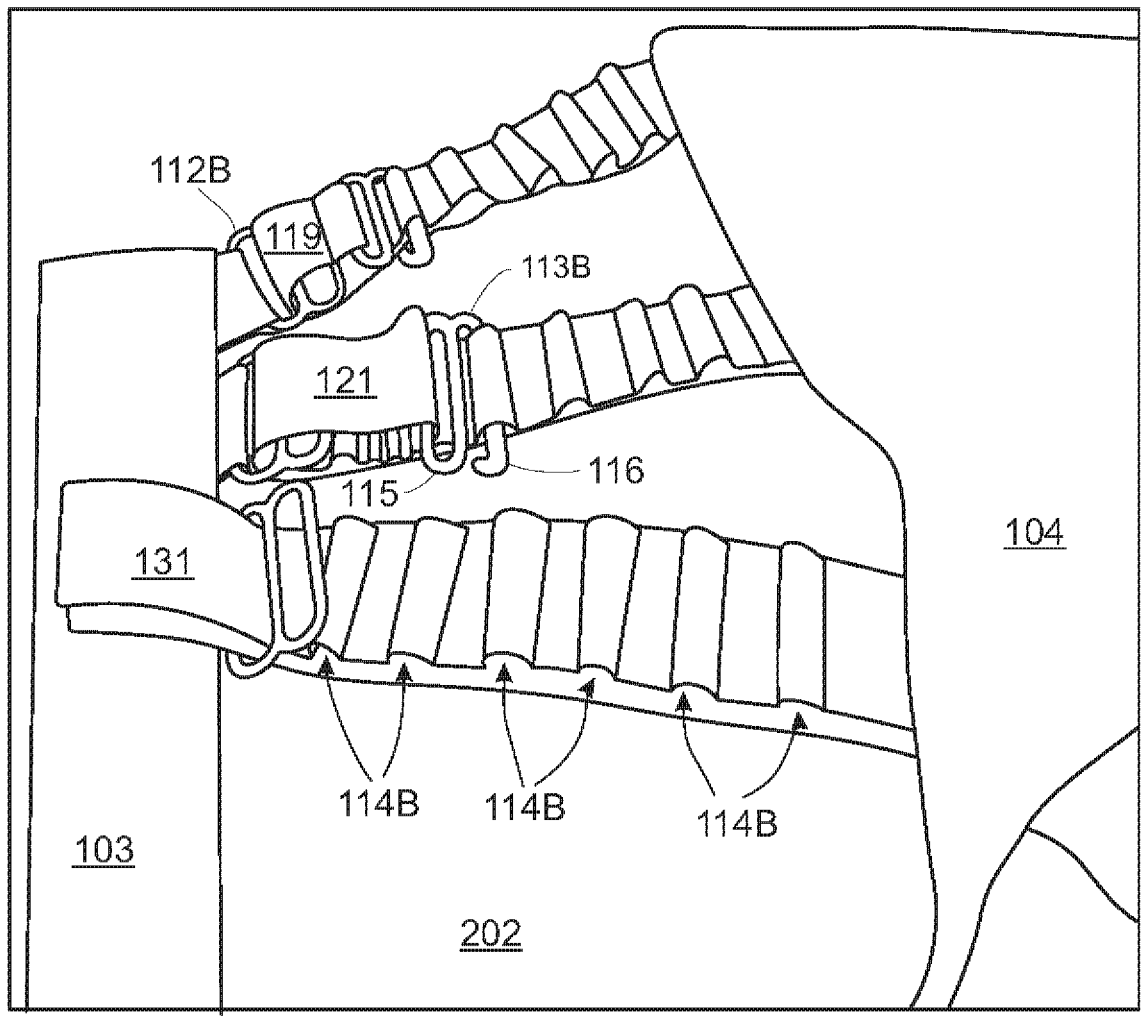
FIG. 2 is a back detailed view of the posture enhancing top according to an embodiment of the present invention.
Figure 3:
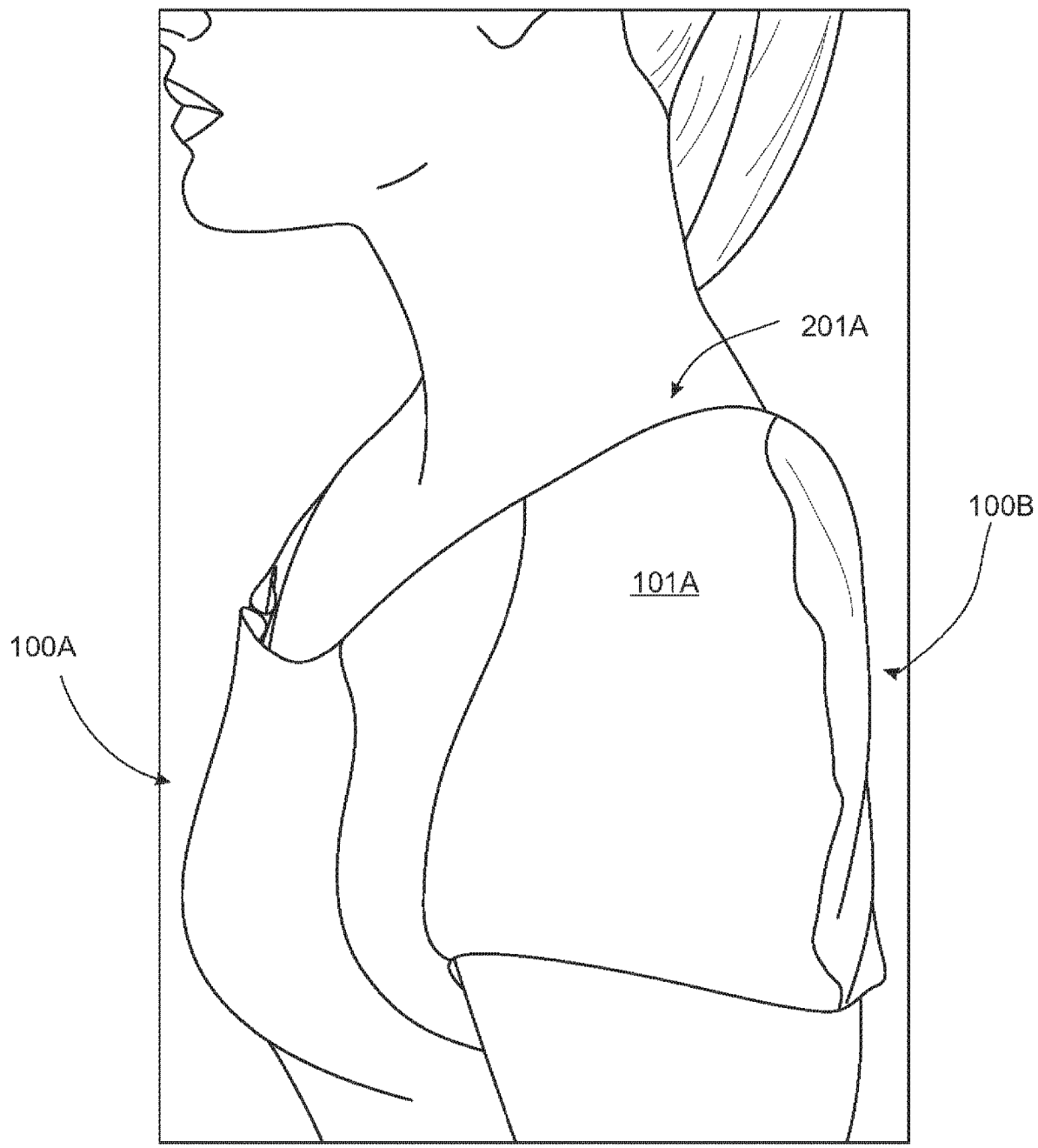
FIG. 3 is a side view of the posture enhancing top according to an embodiment of the present invention.
Figure 4:
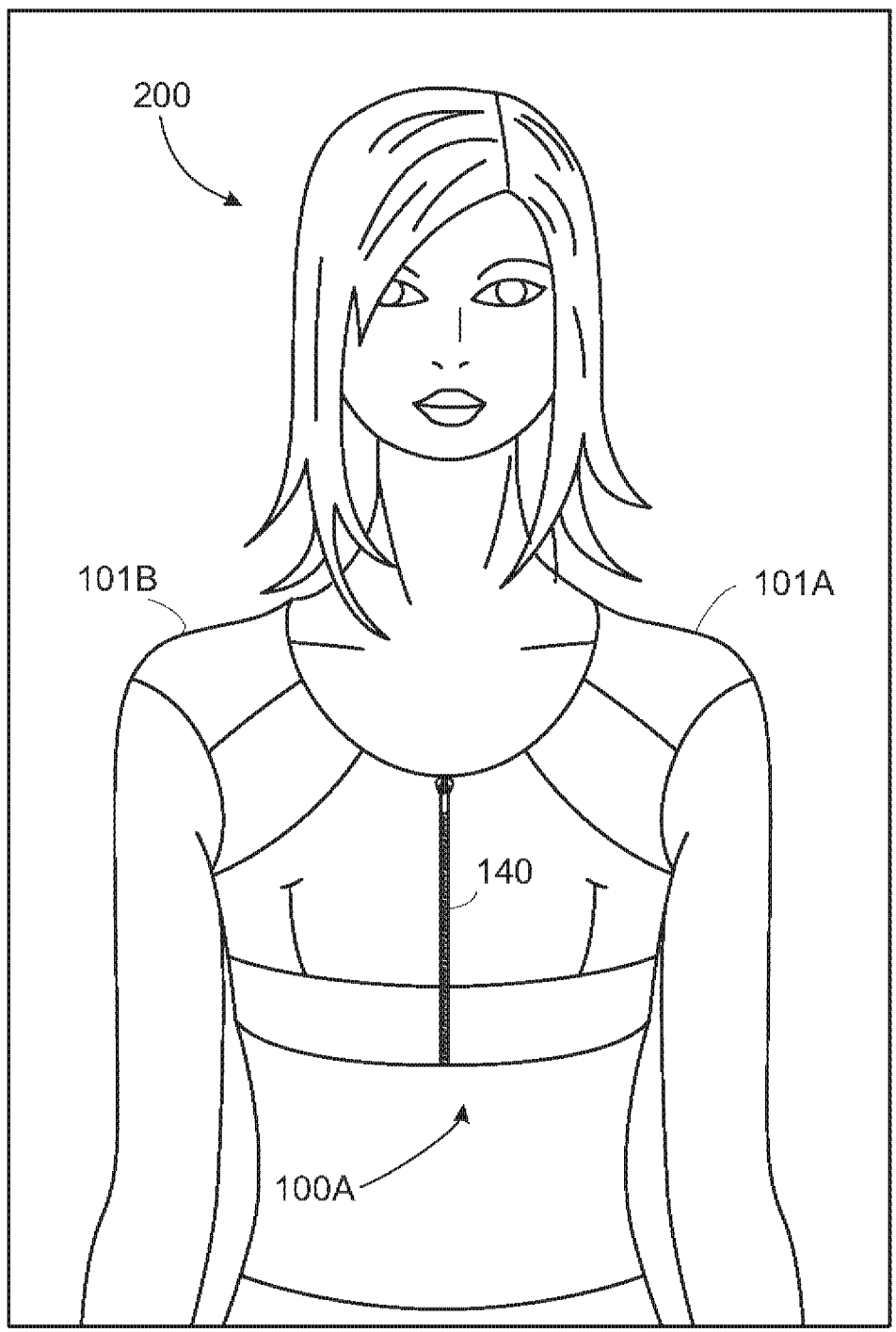
FIG. 4 is a front view of the posture enhancing top according to an embodiment of the present invention.

Referring now to FIGS. 1-2, the right upper strap 110B includes a buckle 112B, a clasp 113B, and several slits 114B along the length of the strap. In one embodiment, the buckle attaches to connecting material 111B, which is connected to the central spine member 103, and facilities the length of the strap with the combination of the clasp, as the clasp includes a hook 116 configured to be positioned in a slit of the several slits. In alternative embodiments, the buckle attaches directly to the central spine member, and no connecting material is provided. The shorter the strap is the more pulling force the strap will provide. As previously mentioned each strap is of similar construction but differs in positioning. For example, the left upper strap also includes a buckle 112A, a clasp 113A, and several slits 114A along the length of the strap. Best seen in FIG. 2, a strap is comprised of a rectangular piece of non-elastic material 131 (as seen on the lower right strap) which is attached to lower shoulder member 104B. The strap includes several slits 114B along the length of the strap. Buckle 112B includes two rings, a first ring attaches the buckle to the central spine 103 and the second ring allows for the strap to reverse directions (seen as material 121 in the middle strap), such that the length of the strap between the lower shoulder member and central spine is reduced. The free end of the strap is attached to a ring 115 on the clasp 113B, which includes hook 116 for engaging a selected slit 114B. It should be understood; the use of the buckles, clasps, and hooks can be replaced with similar components offering the same functionality of adjustment. However, there should be levels of adjustment, i.e. like the slits, and not an overall adjustment such a hook and loop fasteners. The wearer needs to be able to dial in the adjustments, i.e. adjust the length of the strap between the lower shoulder member and central spine to a known amount with no guesswork, such as slits, pockets, or slots. In some embodiments, insignia or markings may be provided near each slit for identification.

In some embodiments, the upper straps 110A and 110B extend within the fabric of the lower shoulder members 104A and 104B and extend to the pair of top shoulder members 101A and 101B. More specifically, the upper strap starts on the anterior part of the shoulder so that pulling force also engages the shoulder and brings it backward, preventing slouching. The straps are located on the scapula and are designed to bring the shoulders closer to the wearer's spine while the posture-enhancing top is worn. In some embodiments, the upper straps are positioned at the upper part of the scapula creating an anatomically correct pull back and down, while the other straps (middle and lower) contribute to reinforcing the pull. The straps and their angles in relation to the shoulders and central spine control the direction of the forces to pull the wearer's shoulders in the ideal position as discussed above.

In one embodiment, lower horizontal band 102 made from elastic material is configured to secure the posture enhancing top on the wearer's body and balance the pulling force of the plurality of straps. In one embodiment, the central spine member 103 is constructed from several layers of non-elastic material providing a rigid element configured to counterbalance the pulling force from the plurality of straps.

In one embodiment, the front portion of the posture enhancing top includes an opening 140 and fastener enabling the wearer to take on and off the posture enhancing top. In some embodiments, the opening is positioned vertically and is configured to traverse the entire height of the posture enhancing top on the front side of the top. In one embodiment, the fastener is a zipper, but it should be understood that other known fasteners may be used, including but not limited to buttons, hook and look fasteners, magnets, etc.

During use, a hook for each strap is positioned in a slit towards the central spine member, such that the length of the strap is the longest. This allows the user to get accustomed to the invention before the lengths of the straps are reduced, increasing the pulling forces on the wearer's shoulders. After the wearer is accustomed to this arrangement (usually around 3 weeks), it is recommended to move the hook to a middle slit, which makes the strap tighter and increases the pulling force. Within another three weeks' time frame, the hook can move onto a third slit with the strongest pull. This example covers a strap with three slits; however the number of slits may vary, and the wearer can continue to reduce the length of the straps (increase the pulling force) until either there are no more slits left, or until their posture is improved via the invention. Finally, the wearer may continue to wear the invention for posture maintenance.

Figure 5:
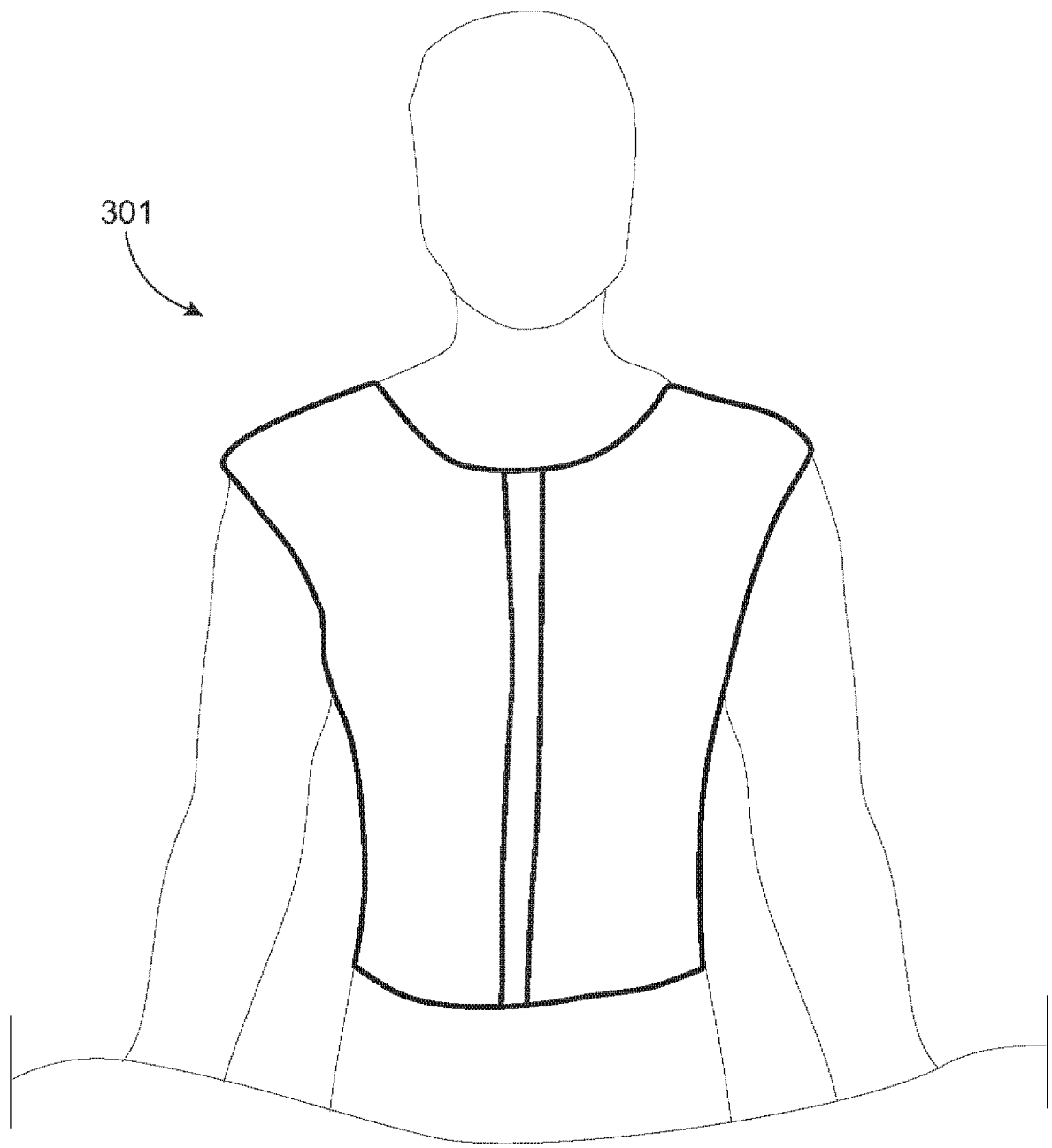
FIG. 5 is a front view of a posture enhancing top designed for a male according to an embodiment of the present invention.
Figure 6:
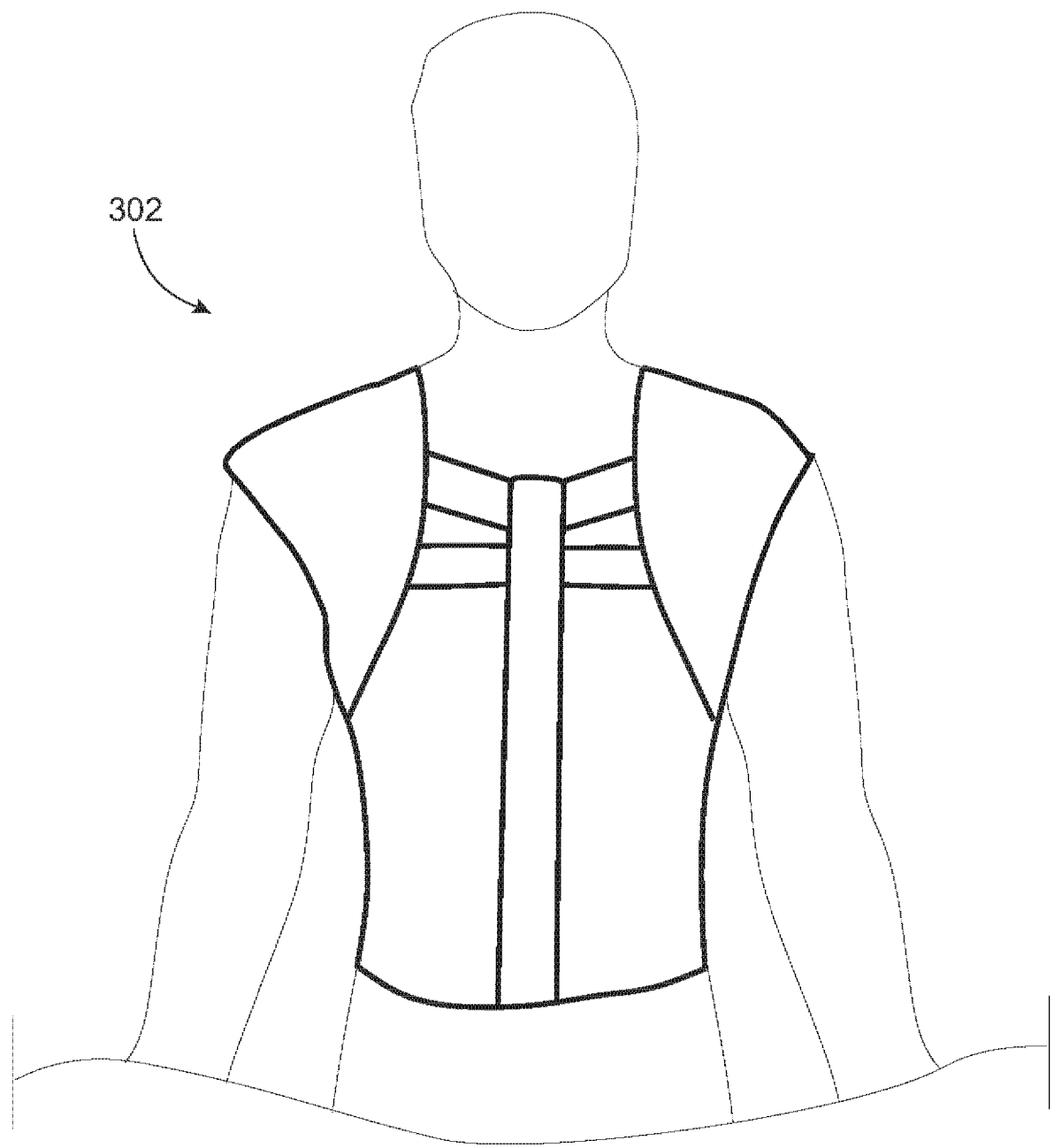
FIG. 6 is a rear view of the posture enhancing top designed for a male according to an embodiment of the present invention.
Figure 7:
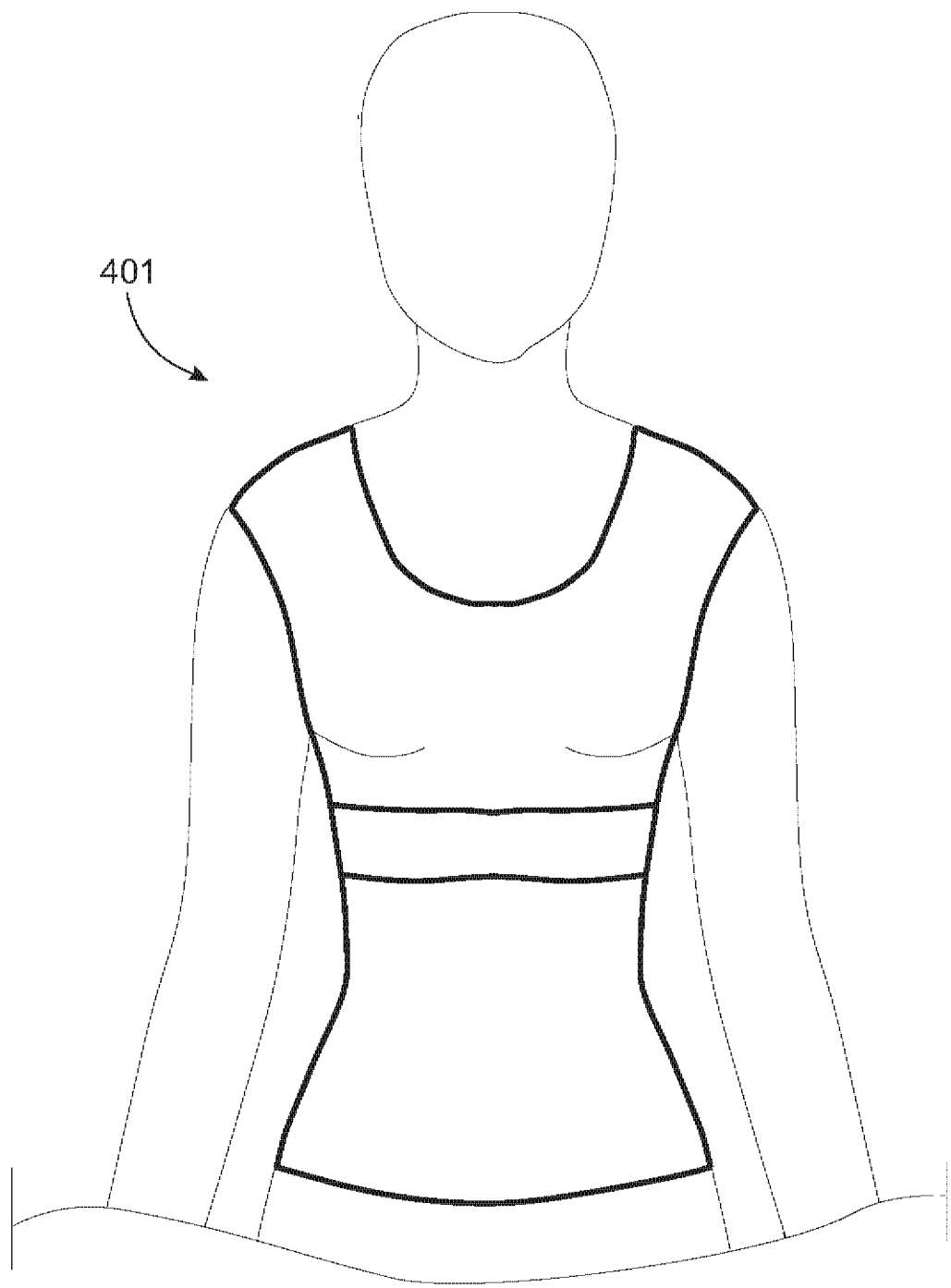
FIG. 7 is a front view of a posture enhancing top designed for a female according to an embodiment of the present invention.
Figure 8:
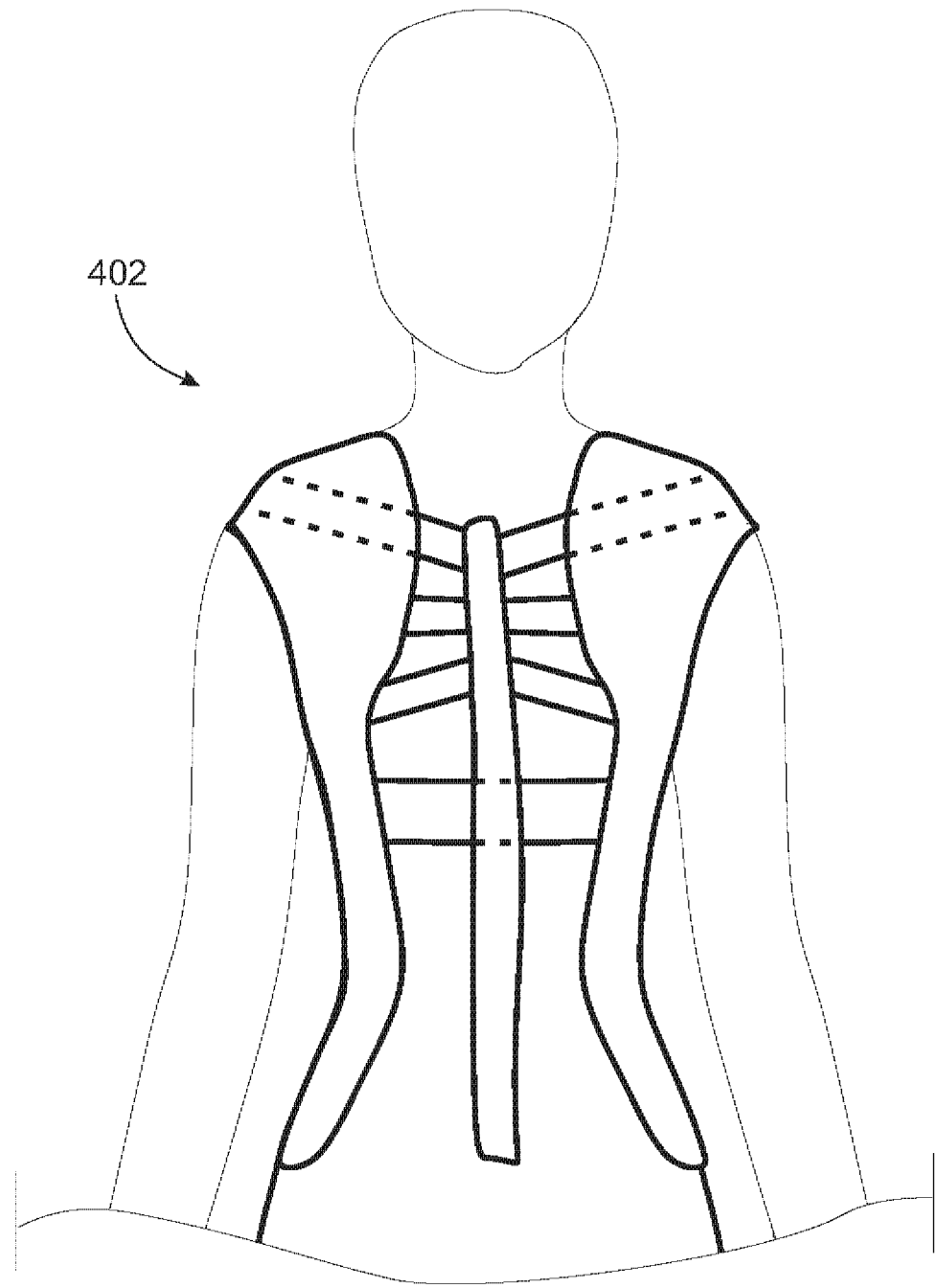
FIG. 8 is a rear view of the posture enhancing top designed for a female according to an embodiment of the present invention.

Advantageously, the present invention is configured to either be a stand-alone top that can be worn under, over, or in lieu of any additional tops, or alternatively, the present invention may be incorporated into existing garments. Some versions of the posture enhancing top can be seen in FIGS. 5-8. FIGS. 5-6 show the front and rear sides of a men's posture enhancing top respectively. In some embodiments, these versions are configured to be incorporated into a garment top. Although it should be understood the design may vary, in the exemplary instance, the men's version is configured to cover a substantial part of the front of the torso, wherein the rear of the top includes a pair of two straps, one horizontal strap pair and one angled strap pair (four total straps). FIGS. 7-8 show the front and rear sides of a females' posture enhancing top respectively. The female version is similar to the male version, however, the female version includes another pair of lower straps (six total straps).

In some embodiments, additional horizontal straps may be included to increase or enhance the horizontal pull in the back, wherein the horizontal strap is configured to be positioned above the breasts, which is most suitable for men's designs.

Figure 9:
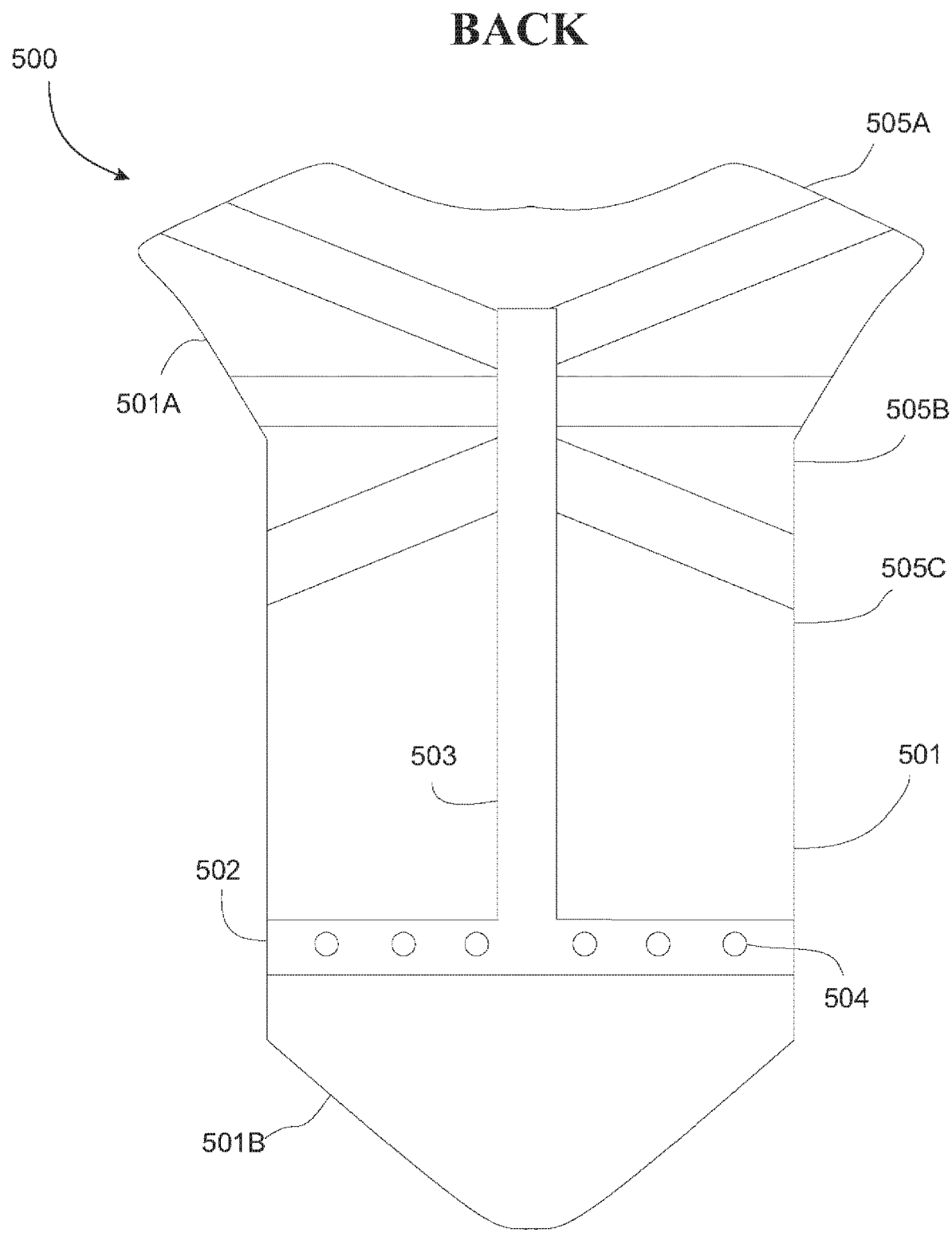
FIG. 9 is a rear view of an alternative posture enhancing bodysuit according to an embodiment of the present invention.

Referring now to FIG. 9, a posture enhancing bodysuit 500 is illustrated. In one embodiment, the posture enhancing bodysuit 500 comprises a bodysuit 501 which includes a top portion 501A and bottom portion 501B, wherein the bottom portion is configured to receive a person's legs similar to underwear as well known in the art. Advantageously, this prevents the top portion 501A from riding up the abdomen during use. In one embodiment, the bodysuit is a single piece. In another embodiment, the top and bottom portion or two separate pieces. A plurality of metallic snaps 503 along the elastic waste band 502 can either connect the two separate pieces or may be used to size the waist portion in the single piece version. The remaining elements, including the central spine member 503 and straps 505A-C are as described in previous embodiments.

Advantageously, the present invention stimulates scapula adduction by using the adjustable straps in optimal angles and promotes shoulder opening. As a result, the wearer takes an upright position. As well known in the art, the shoulder consists of four joints: sternoclavicular (SC), acromioclavicular (AC), and scapulothoracic joints, and glenohumeral joint. When one of these joints moves, others follow. For example, when scapula adducts, shoulders follow this move posteroinferiorly and, as a result, the person goes into a more upright posture. When shoulders and scapula protract (moves forward), one finds themselves in a slouched position. If this position is habitual mid trapezius and rhomboid muscles become elongated and, quite possibly, weak. Though rewriting already existing habits is extremely difficult, the present invention can successfully establish new habits over a period of time. One starts wearing the present invention when straps are in the longest position. Though this position doesn't create any pull yet, it's crucially important for the wearer to get accustomed to feeling a gentle hold of their back. Once the wearer is accustomed to the hold, they can adjust and tighten (reduce the length) the strap to initiate more tension. This activates previously elongated mid trapezius and rhomboid muscles. As they reduce the length and tighten the strap, the straps shorten and so do the activated mid trapezius and rhomboid muscles. Their gradual shortening gradually loads them with more work. Since it all happens over a certain period of time, our body goes into a new habit with ease. Though the invention gives an immediate posture enhancing effect to the wearer, the real benefit of long-term posture correction happens through the continuous wearing of overtime. Muscle memory remembers more optimal positioning. According to research, neurological adaptation happens after two to four weeks of training. Wearing the present invention is similar to low-load resistance training in the sense that the wearer's body will have to hold the pull and develop resistance against it.

Although the invention has been described in considerable detail in language specific to structural features, it is to be understood that the invention defined in the appended claims is not necessarily limited to the specific features described. Rather, the specific features are disclosed as exemplary preferred forms of implementing the claimed invention. Stated otherwise, it is to be understood that the phraseology and terminology employed herein, as well as the abstract, are for the purpose of description and should not be regarded as limiting. Therefore, while exemplary illustrative embodiments of the invention have been described, numerous variations and alternative embodiments will occur to those skilled in the art. Such variations and alternate embodiments are contemplated and can be made without departing from the spirit and scope of the invention.

It should further be noted that throughout the entire disclosure, the labels such as left, right, front, back, top, bottom, forward, reverse, clockwise, counterclockwise, up, down, or other similar terms such as upper, lower, aft, fore, vertical, horizontal, oblique, proximal, distal, parallel, perpendicular, transverse, longitudinal, etc. have been used for convenience purposes only and are not intended to imply any particular fixed direction or orientation. Instead, they are used to reflect relative locations and/or directions/orientations between various portions of an object.

In addition, reference to "first," "second," "third," and etc. members throughout the disclosure (and in particular, claims) are not used to show a serial or numerical limitation but instead are used to distinguish or identify the various members of the group.

What is claimed is:

1. A posture enhancing top comprising:
   a pair of top shoulder members;
   a pair of lower shoulder members, wherein the pair of top shoulder members are configured to cover and engage a wearer's superior shoulder area from the clavicle to humerus insertion and the pair of lower shoulder members are configured to cover and engage the posterior shoulder area of the wearer's shoulders leaving the lateral shoulder area substantially unrestricted such that movement in the wearer's shoulder joint is possible;
   a lower horizontal band configured to encircle the wearer's torso;
   a central spine member extending vertically from the lower horizontal band, wherein the central spine member is configured to be positioned along the wearer's spine constructed from several layers of non-elastic material forming a rigid element;
   a plurality of straps consisting of an upper left strap, an upper right strap, a middle left strap, a middle right strap, a lower left strap, and a lower right strap, wherein the upper left strap and the upper right strap each have a first end and a second end, wherein the first ends are configured to attach to the central spine member and the second ends are configured to extend within the pair of lower shoulder members to the pair of top shoulder members corresponding to a front portion of the posture enhancing top and the end of the wearer's clavicle;
   the middle left strap, the middle right strap, the lower left strap, and the lower right strap are constructed from a non-elastic material and configured to attach to the central spine member on one end and a lower shoulder member of the pair of lower shoulder members on an opposite end, wherein each strap of the plurality of straps is adjustable in length such that the length between the central spine member and the pair of top shoulder members and the pair of lower shoulder members is configured to be reduced via a pulling force of the wearer's shoulders backwardly and downwardly towards the wearer's spine and scapula adduction improving the wearer's posture; and,
   wherein the central spine member is configured to counterbalance the pulling force from the plurality of straps.

2. The posture enhancing top of claim 1, wherein the pair of top shoulder members, the pair of lower shoulder members, the lower horizontal band are constructed from elastic material.

3. The posture enhancing top of claim 1, wherein the upper left strap and the upper right strap are positioned at an upper part of the scapula creating an anatomically correct backwardly and downwardly pulling force, while the middle left strap, the middle right strap, the lower left strap and the lower right strap contribute to reinforcing the pulling force of the upper left strap and the upper right strap.

4. The posture enhancing top of claim 1, wherein each strap of the plurality of straps comprises a number of slits configured to enable the adjustment in length of each strap.

5. The posture enhancing top of claim 1, further comprising a front portion connected to the pair of top shoulder members, the pair of lower shoulder members, and the lower horizontal band, wherein the front portion includes an opening and fastener enabling the wearer to take on and off the posture enhancing top.

6. The posture enhancing top of claim 5, wherein the front portion is constructed from an elastic material.

7. The posture enhancing top of claim 1, wherein the upper left strap and the upper right strap are angled upwards towards the pair of top shoulder members from the central spine member, the middle left strap and the middle right strap extend from the central spine member to the pair of lower shoulder members, and the lower left strap and the lower right strap are angled downwardly from the central spine member to the pair of lower shoulder members.

\* \* \* \* \*